United States Patent
Hall et al.

(10) Patent No.: US 6,892,999 B2
(45) Date of Patent: May 17, 2005

(54) PROBE ACTIVATED VALVE SYSTEM

(75) Inventors: Bernard Hall, London (CA); Daniel McGill, St. Marys (CA); John Vanderhayden, St. Thomas (CA)

(73) Assignee: Checkfluid Inc., London (CA)

( * ) Notice: Subject to any disclaimer, the term of this patent is extended or adjusted under 35 U.S.C. 154(b) by 75 days.

(21) Appl. No.: 10/294,617

(22) Filed: Nov. 15, 2002

(65) Prior Publication Data

US 2003/0089874 A1 May 15, 2003

Related U.S. Application Data

(60) Provisional application No. 60/331,403, filed on Nov. 15, 2001.

(51) Int. Cl.[7] .............................................. F16K 51/00
(52) U.S. Cl. ............................ 251/149.5; 251/149.6; 251/357
(58) Field of Search .................... 251/149.4, 149.5, 251/149.6, 357, 360, 363

(56) References Cited

U.S. PATENT DOCUMENTS

| | | | |
|---|---|---|---|
| 1,626,729 A | | 5/1927 | Handlan, Jr. |
| 1,865,231 A | | 6/1932 | Buck |
| 2,024,682 A | | 12/1935 | Eisenman |
| 2,618,978 A | | 11/1952 | Ragland |
| 2,730,382 A | * | 1/1956 | De Mastri ............... 251/149.6 |
| 3,129,919 A | * | 4/1964 | Evans ..................... 251/149.4 |
| 3,160,182 A | | 12/1964 | O'Donnell |
| 3,164,361 A | | 1/1965 | Pruett |
| 3,715,099 A | * | 2/1973 | Shendure ................. 251/149.6 |
| 3,794,289 A | | 2/1974 | Taylor |
| 3,807,687 A | * | 4/1974 | Thompson ............... 251/149.4 |
| 3,836,114 A | * | 9/1974 | Norton et al. ........... 251/149.6 |
| 4,005,847 A | | 2/1977 | Ekman |
| 4,060,219 A | * | 11/1977 | Crawford ................. 251/149.6 |
| 4,070,003 A | * | 1/1978 | Shames et al. .......... 251/149.6 |
| 4,354,523 A | | 10/1982 | Hochmuth et al. |
| 4,366,945 A | * | 1/1983 | Blauenstein ............. 251/149.6 |
| 4,476,892 A | * | 10/1984 | Boyce ..................... 251/149.6 |
| 4,530,421 A | * | 7/1985 | Balch ...................... 251/149.6 |
| 4,593,713 A | | 6/1986 | Menshen |
| 4,612,953 A | * | 9/1986 | Caroll et al. ............. 251/149.6 |
| 4,638,668 A | | 1/1987 | Leverberg et al. |
| 4,699,356 A | | 10/1987 | Hargrove et al. |
| 4,699,387 A | | 10/1987 | Buseth |
| 4,745,950 A | * | 5/1988 | Mathieu .................. 251/149.6 |
| 4,792,115 A | * | 12/1988 | Jindra et al. ............ 251/149.6 |

(Continued)

FOREIGN PATENT DOCUMENTS

| | | |
|---|---|---|
| DE | 582 136 C | 8/1933 |
| DE | 25 32 275 A | 2/1977 |
| EP | 1043526 A2 | 10/2000 |
| FR | 619 655 A | 4/1927 |
| FR | 1 403 103 A | 6/1965 |
| GB | 2348257 A | 9/2000 |

*Primary Examiner*—John Bastianelli
(74) *Attorney, Agent, or Firm*—Dilip C. Andrade; Borden Ladner Gervais LLP

(57) ABSTRACT

A probe activated valve system is disclosed that permits easier and safer testing of fluids in a pressurized system. The system has a shell having a valve passage. The valve passage has an end through which the valve passage is fluidly connected to a probe passage. A valve seat is provided at the end of the valve passage. A valve sealing member forms a face seal against the valve seat by compressing a retained sealing member, such as an O-ring. The valve sealing member is moveable from a closed position to an open position, upon insertion of a probe to engage and displace the valve sealing member along the valve passage, such that the valve sealing member is spaced from the valve seat and allows fluid in the valve passage to flow to the probe passage for collection by the probe.

19 Claims, 12 Drawing Sheets

U.S. PATENT DOCUMENTS

| | | | | |
|---|---|---|---|---|
| 4,825,893 A | * | 5/1989 | Gailey | 251/149.6 |
| 4,962,881 A | | 10/1990 | Otsuki et al. | |
| 5,079,962 A | | 1/1992 | Peterson, Jr. | |
| 5,294,092 A | * | 3/1994 | Wade et al. | 251/149.6 |
| 5,490,680 A | | 2/1996 | Patel et al. | |
| 5,738,144 A | * | 4/1998 | Rogers | 251/149.4 |
| 5,901,686 A | | 5/1999 | Stockner et al. | |
| 6,056,163 A | | 5/2000 | Lai | |
| 6,279,874 B1 | * | 8/2001 | Nyberg | 251/149.6 |
| 6,330,890 B1 | | 12/2001 | Ekman | |

\* cited by examiner

PROBE ACTIVATED VALVE SYSTEM

The present application claims the benefit of priority from U.S. provisional patent application No. 60/331,403 filed on Nov. 15, 2001.

FIELD OF THE INVENTION

The present invention relates to valve systems and particularly to probe activated valve systems.

BACKGROUND OF THE INVENTION

The present invention is directed to a probe activated valve system. Current probe activated valve systems are typically comprised of a valve sealing member, possibly with a ball or hemispherical end, which is pressed against a sealing element or against a metal seat. Alternatively a ball is pressed against the seal or seat by a spring or headed valve sealing member and spring arrangement. Another sealing element, contained by a separate insert, is used to prevent leakage on the outside of the probe when the valve is open. Alternate current designs for accessing fluid or gas, typically pressurized, include designs outlined in ISO 15171-1, ISO 15171-2 and other proprietary designs.

The purpose of these devices is to allow sampling to determine the physical and chemical elements of the fluid in a system. For example, these devices allow the determination of physical properties of fluid in a system such as temperature and pressure. Chemical properties such as viscosity and acidity can also be determined. For example, it may be important to know the amount of contaminant particulate within a system or be aware of wear metals in a system with moving parts such as an engine. Contaminant particulate is a leading cause of incomplete combustion, environmental air pollution, and premature failure in pressurized lubrication and cooling systems.

A problem with existing valve systems is that they may not provide an adequate seal. For example, a metal on metal seal formed by a ball valve cooperating with a valve seat can result in weepage if the ball or seat contain imperfections or are not perfectly spherical. Imperfections may be created during operation, such as brinelling caused by hydraulic spikes. Even if a proper seal initially exists, the ball can be rotated during probing with an imperfect seal arising following reseating of the ball. Even if the ball is spherical, contaminants from the system can accumulate on the ball and valve seat to impair the seal. External contaminants can also be introduced during the sampling process by insertion of the probe.

Other valves, such as a tire style valve have an elastomeric element to form a barrel seal. However, the structure of a tire style valve includes a pin which can be bent or deformed from high pressure in the system arising from, for example, a pressure spike. Other seals having an elastomeric element, such as a barrel style O-ring, can fail when there is high turbulence in the valve resulting in washing out or displacement of the sealing element. This washing out can also take place if the valve is used to fill or replace system fluids. Other elastomeric seal types require additional retaining members to securely capture the sealing element.

Furthermore, apart from a compromised seal, another problem associated with conventional probe activated valves is user safety in systems under high pressure. For example, systems using probe activated valves can be pressurized from 2000 to 10000 psi which may not be a desirable or safe level of pressure to which a hand probe user should be exposed. A hand inserted probe is limited by the finger or thumb strength of the user which in the present invention is in the range of 500 to 1500 psi. However, due to the surface area and geometry of a conventional valve sealing member, such as a ball in a ball valve, the pressure required to open a valve can be significantly less than the pressure of the system, thereby exposing a user to an unexpected and potentially injurious hazard.

SUMMARY OF THE INVENTION

It is an object of the present invention to obviate or mitigate at least one disadvantage of prior art valve systems.

According to an aspect of the present invention, there is provided According to an aspect of the present invention, there is provided a probe activated valve system comprising a shell having a valve passage, the valve passage having an end through which the valve passage is fluidly connected to a probe passage; a valve seat at the end of the valve passage; a valve sealing member having a retained sealing member; the valve sealing member moveable from a closed position in which the valve sealing member compresses the mechanically retained sealing member against the valve seat to form a face seal and prevents fluid in the valve passage from flowing to the probe passage, to an open position, upon insertion of a probe to engage and displace the valve sealing member along the valve passage, such that the valve sealing member is spaced from the valve seat and allows fluid in the valve passage to flow to the probe passage for collection by the probe.

Preferably, the the valve seat is a stop integrally formed on the shell. The valve system can also include an insert member provided at the end of the valve passage, the insert member having a head, the valve seat being provided on the head, and/or biasing means normally urging the valve sealing member to the closed position. The retained sealing member preferably comprises an elastomeric material, and is an O-ring. Preferably, the valve sealing member includes a groove and the retained sealing member is retained in the groove by mechanical forming, and the valve sealing member is retained in the groove by coining, rolling or a pressing operation. Preferably, the valve system works inline with a valve controlling the main passage creating a twin valve system, which utilizes the same spring. In a further embodiment, a recess is provided in the valve sealing member for aligning the inserted probe with the valve sealing member. In a further embodiment, the probe is permanently fixed to the valve sealing member, such as by frictional engagement with a recess in the valve sealing member, or by threaded engagement with a recess in the valve sealing member. In a preferred embodiment, the valve sealing member and biasing means prevent activation of the valve system by manual forces alone without mechanical advantage against a potentially unsafe system pressure. The shell can also include threaded means for cooperation with corresponding threaded means on a collar to activate the probe, by means of mechanical advantage to allow high pressure fluid in the valve passage to flow to the probe passage.

In a further aspect of the present invention, there is provided a probe activated valve system comprising a shell having a valve passage, the valve passage having an end through which the valve passage is fluidly connected to a probe passage; a valve seat at the end of the valve passage; a valve sealing member having a retained sealing member; the valve sealing member moveable from a closed position in which the valve sealing member compresses the mechanically retained sealing member against the valve seat to form a face seal and prevents fluid in the valve passage from flowing to the probe passage, to an open position, upon insertion of a probe to engage and displace the valve sealing member along the valve passage, such that the valve sealing member is spaced from the valve seat and allows fluid in the probe passage to flow to the valve passage.

Advantageously, the valve system of the present invention provides a secure seal under high system pressure with no weepage and insignificant seepage. The valve sealing member is resistant to the effects of turbulence within the system, specifically, displacement of an elastomeric sealing element such as an O-ring. The valve sealing member also resists damage resulting from the introduction of contaminants during the sampling process.

Other aspects and features of the present invention will become apparent to those ordinarily skilled in the art upon review of the following description of specific embodiments of the invention in conjunction with the accompanying drawings.

BRIEF DESCRIPTION OF THE DRAWINGS

Embodiments of the present invention will now be described, by way of example only, with reference to the attached drawings, wherein.

DETAILED DESCRIPTION

Figure 1:
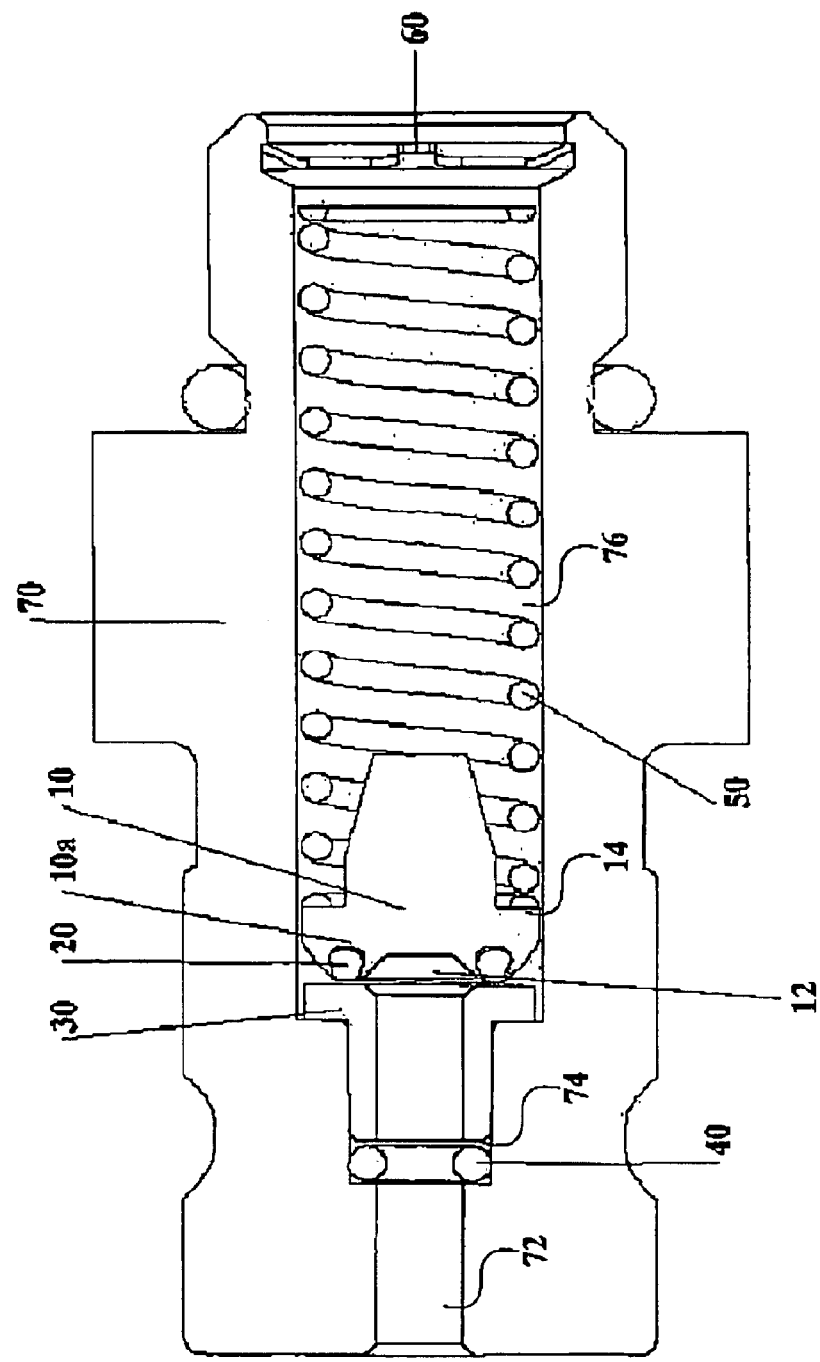
FIG. 1 illustrates a sectional view of a valve system according to an embodiment of the present invention in which the valve is closed.
Figure 1A:
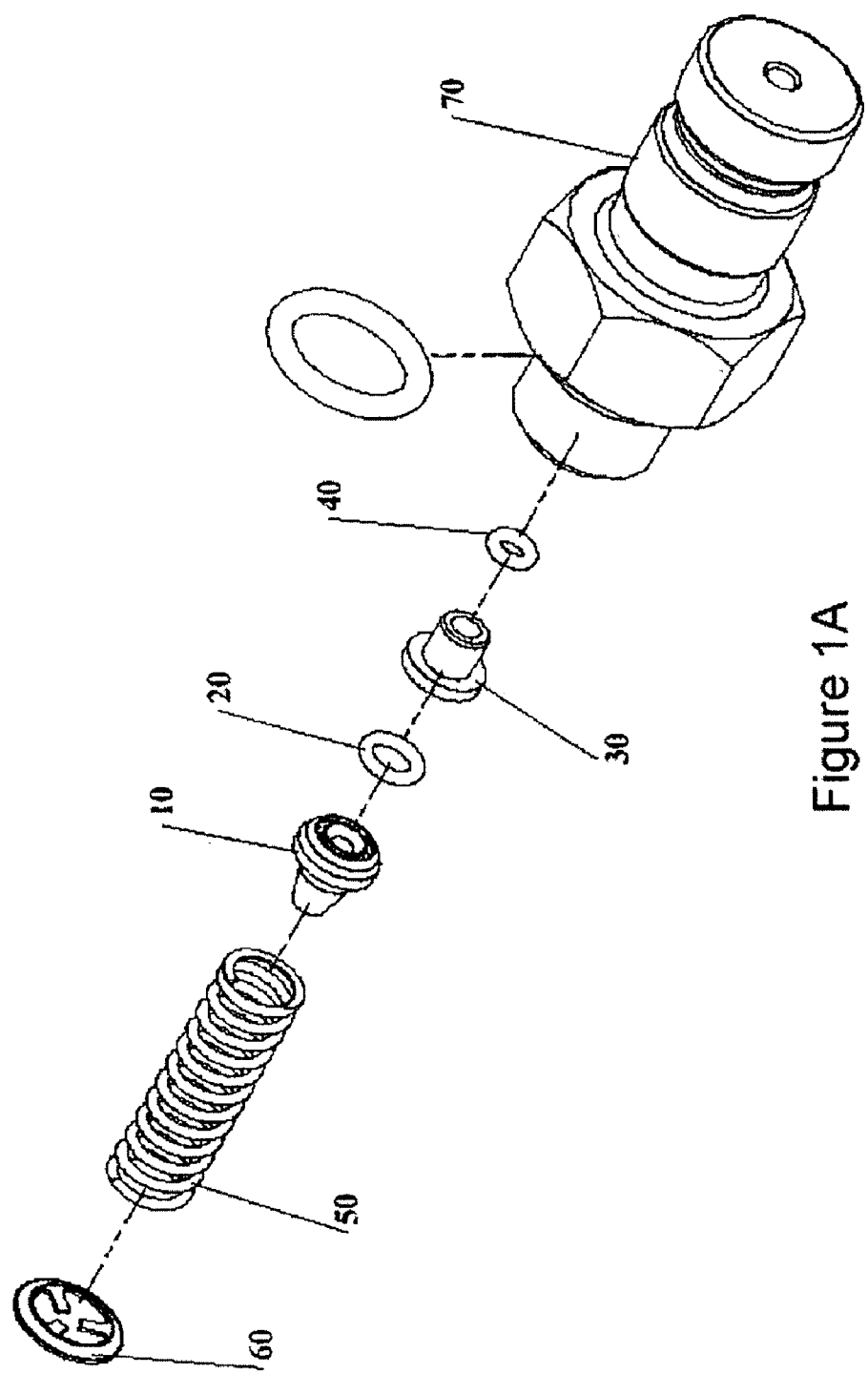
FIG. 1a is an exploded view of the valve system of FIG. 1.

The present invention is a probe activated valve system. FIG. 1 illustrates a probe activated valve system according to an embodiment of the present invention. In FIG. 1, a shell part of a nipple is indicated at 70. The nipple of FIG. 1 is typically installed in a sampling port of a system or machine, such as an engine, to allow sampling of the fluid medium within the fluid circuit in the device. One or more sampling ports can be present in a system or machine depending on the machine's size and function. The fluid can be sampled to determine physical properties of the fluid such as fluid pressure within the circuit and chemical properties of the fluid such as its composition and the presence of contaminants.

The nipple shell 70 has a shell passage 76 which narrows to an intermediate passage 74 and extends to form a probe passage 72. The shell contains a valve system having an insert 30 and a valve sealing member 10. The enlarged head of the insert 30 forms a valve seat in the present example embodiment. However, as an alternative, the shoulder (or stop or vertically extending portion of the shell) between the shell passage 78 and intermediate passage 74 on which the insert 30 as seated can also act as a valve seat. In that situation, the valve sealing member 10 would engage directly with a valve seat formed on the shoulder.

Cooperating with the insert is valve sealing member 10. The head 10a of the valve sealing member 10, serves as a guide during movement of valve sealing member 10 within cylindrical passage in shell 70. The stem of the valve sealing member 10 is used to retain alignment with a spring 60. The force of the spring 50 resists vacuum pressure. In the present example embodiment, the head 10a of the valve sealing member 10 is provided with a recess 12. The head 10a of the valve sealing member 10 is also provided with a retained elastomeric sealing element, such as an O-ring 20. The sealing element 20 is preferably situated in an annular groove in the front face of the head 10a of the valve sealing member 10, but can also be placed in the back face of the insert 30. The sealing element 20 is secured to the valve sealing member 10, for example, by capturing the sealing element 20 through a mechanical pressing operation, such as coining or rolling. The back 14 of the head 10a of the valve sealing member 10a is flat and in combination with the diameter of the head 10a extending to nearly fill cross section of the valve passage, ensures that the system pressure is exerted on the valve sealing member 10. Accordingly, the valve sealing member 10 cannot be easily accidentally displaced when the system is pressurized. By contrast, the ball in a ball valve can be easily unseated even when the system is pressurized because of the geometry involved.

The valve system shown in FIG. 1 is in a closed position. Biasing means, such as coil spring 50, in conjunction with system pressure normally urges the valve closed. In the closed position, the valve sealing member 10 compresses O-ring 20 against the insert 30 to form a face seal. The use of the retained elastomeric sealing element 20 in the present invention enables high repeatability of the functioning of the valve system and allows the present invention to resist the detrimental effects of contaminants present in metal to metal seals.

The size of the valve sealing member 10 can be configured so that if there are high pressures in the system, typically greater than 1500 psi, the valve will remained closed when a hand operated probe, with no mechanical advantage, is applied.

Figure 3:
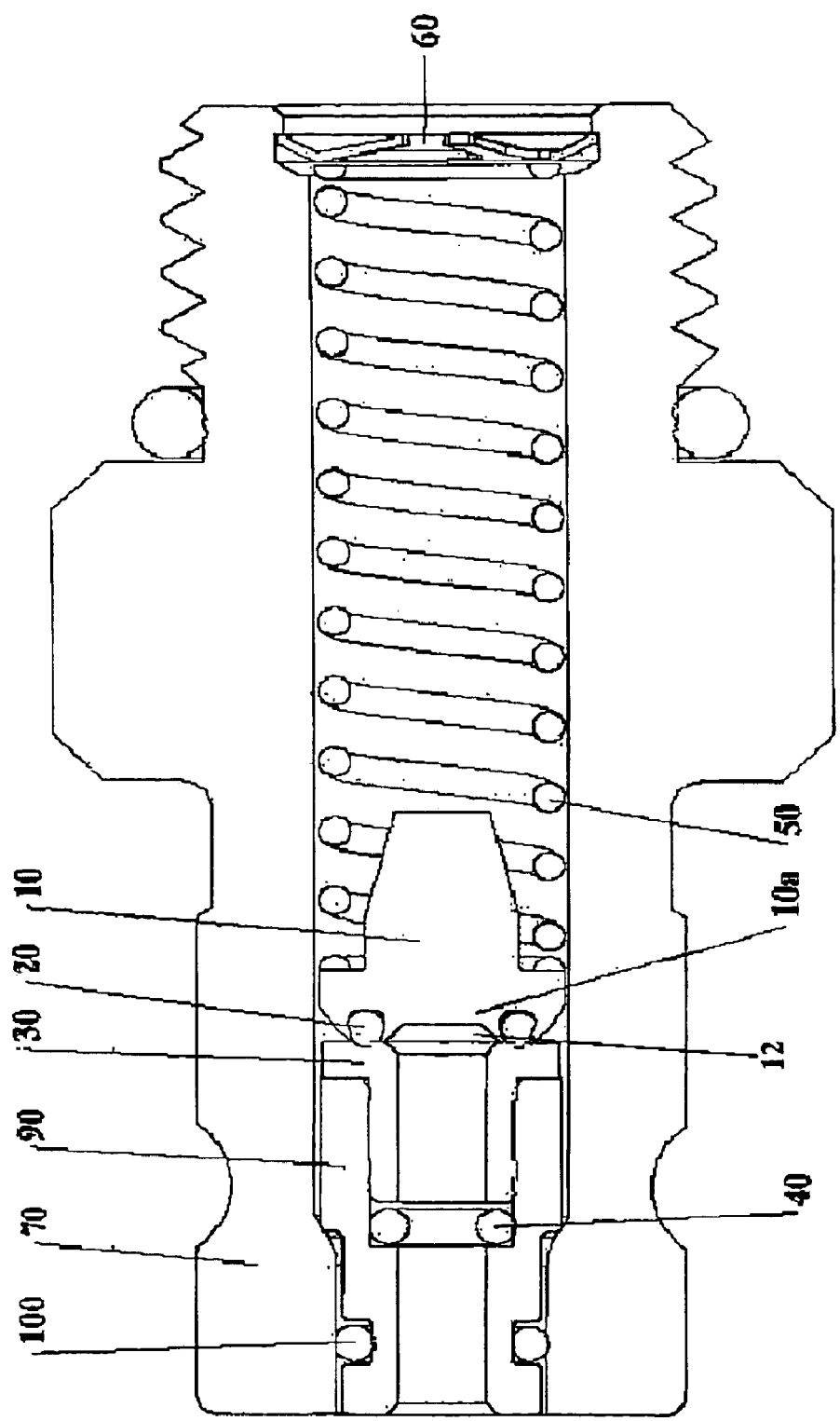
FIG. 3 illustrates a section view of a valve system according to a twin valve embodiment of the present invention.
Figure 3A:
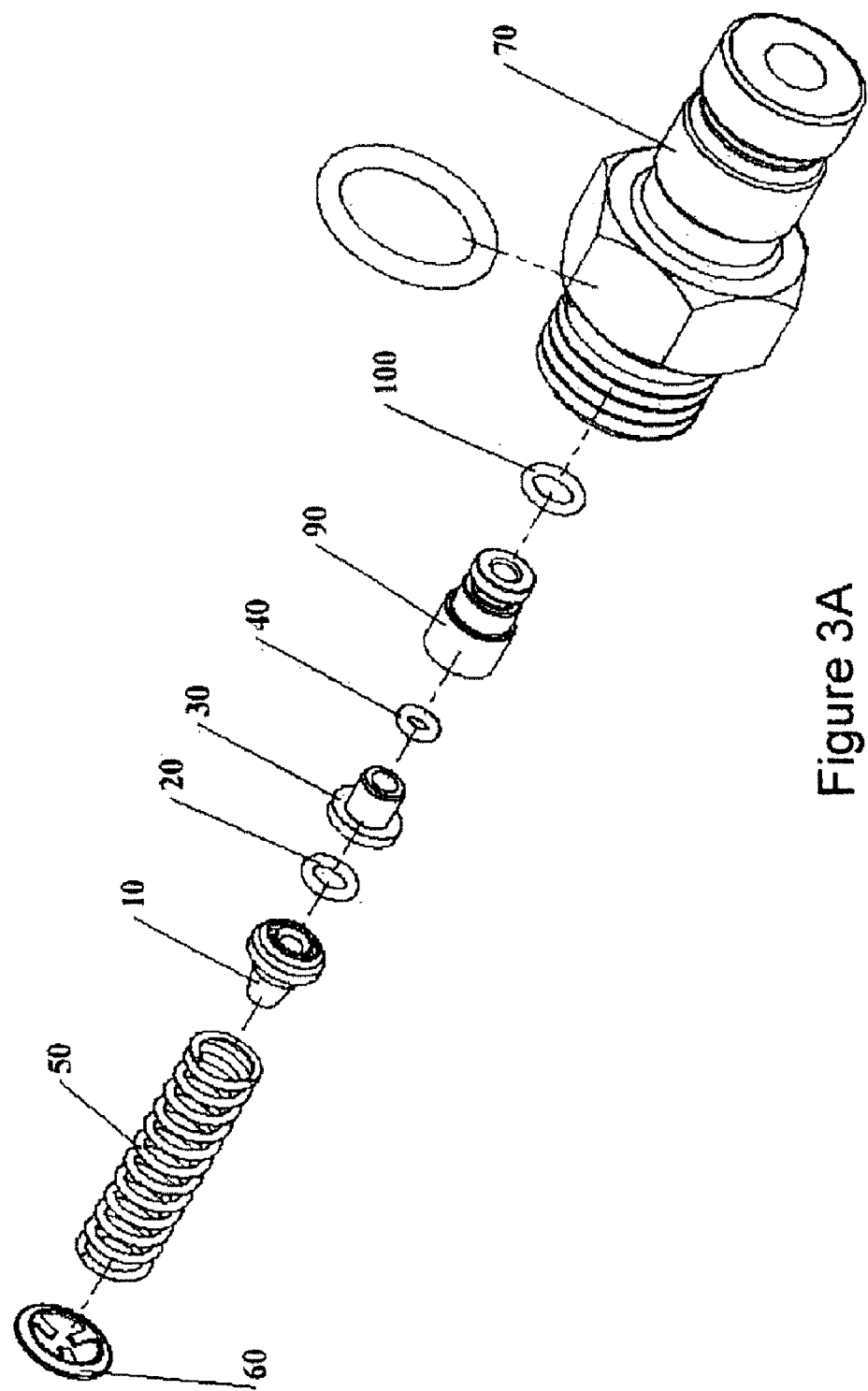
FIG. 3a is an exploded view of the valve system of FIG. 3.
Figure 6:
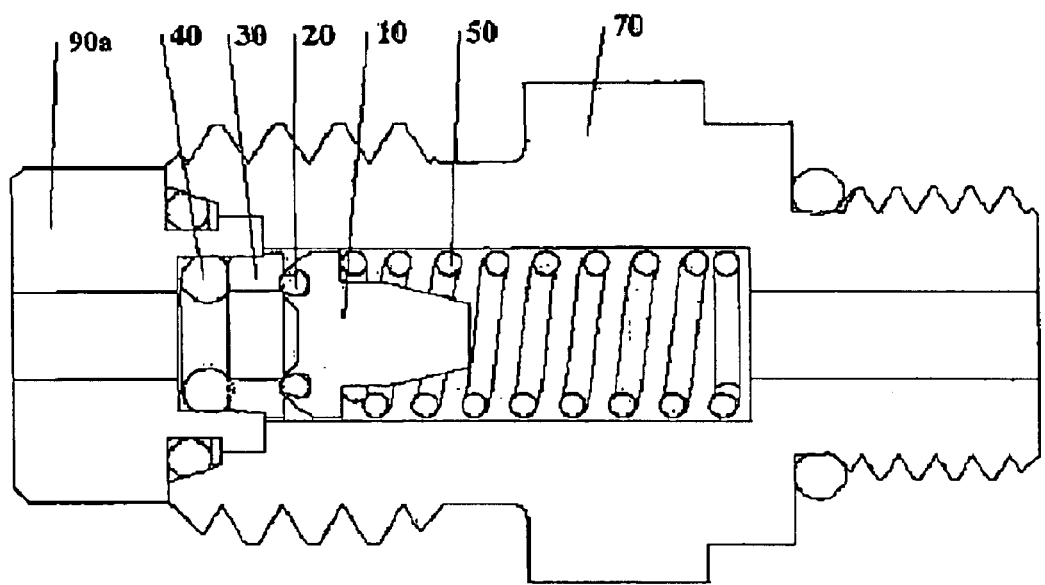
FIG. 6 illustrates a longitudinal view of a valve system according to a further embodiment of the present invention.
Figure 6A:
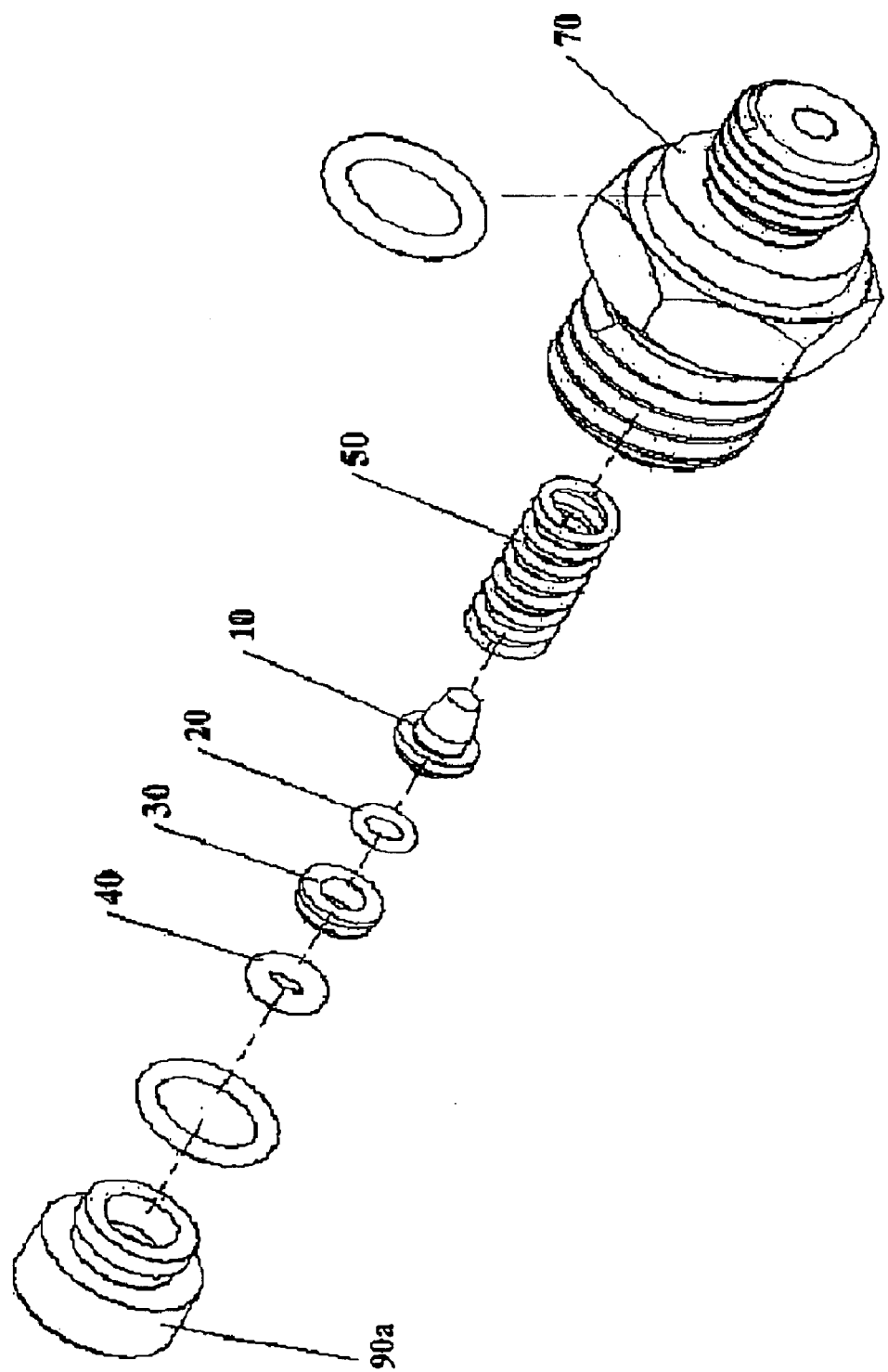
FIG. 6a is an exploded view of the valve system of FIG. 6.

The insert 30 may be either threaded into place or, alternately, held by friction in the shell 70 or other valve component 90 (in multi-port valves FIG. 3, or valves assembled from the coupling end FIG. 6). As shown in FIG. 1, the insert 30 can be used to retain a second sealing element 40, for example, by pressing it against a shoulder of the valve passage (shown in FIG. 1). An annular washer 60 is used to retain the spring 50. Alternatively, if the valve system is assembled from the coupling end as shown in FIG. 6, a stop provided in the body itself can be used to contain the spring.

Figure 2:
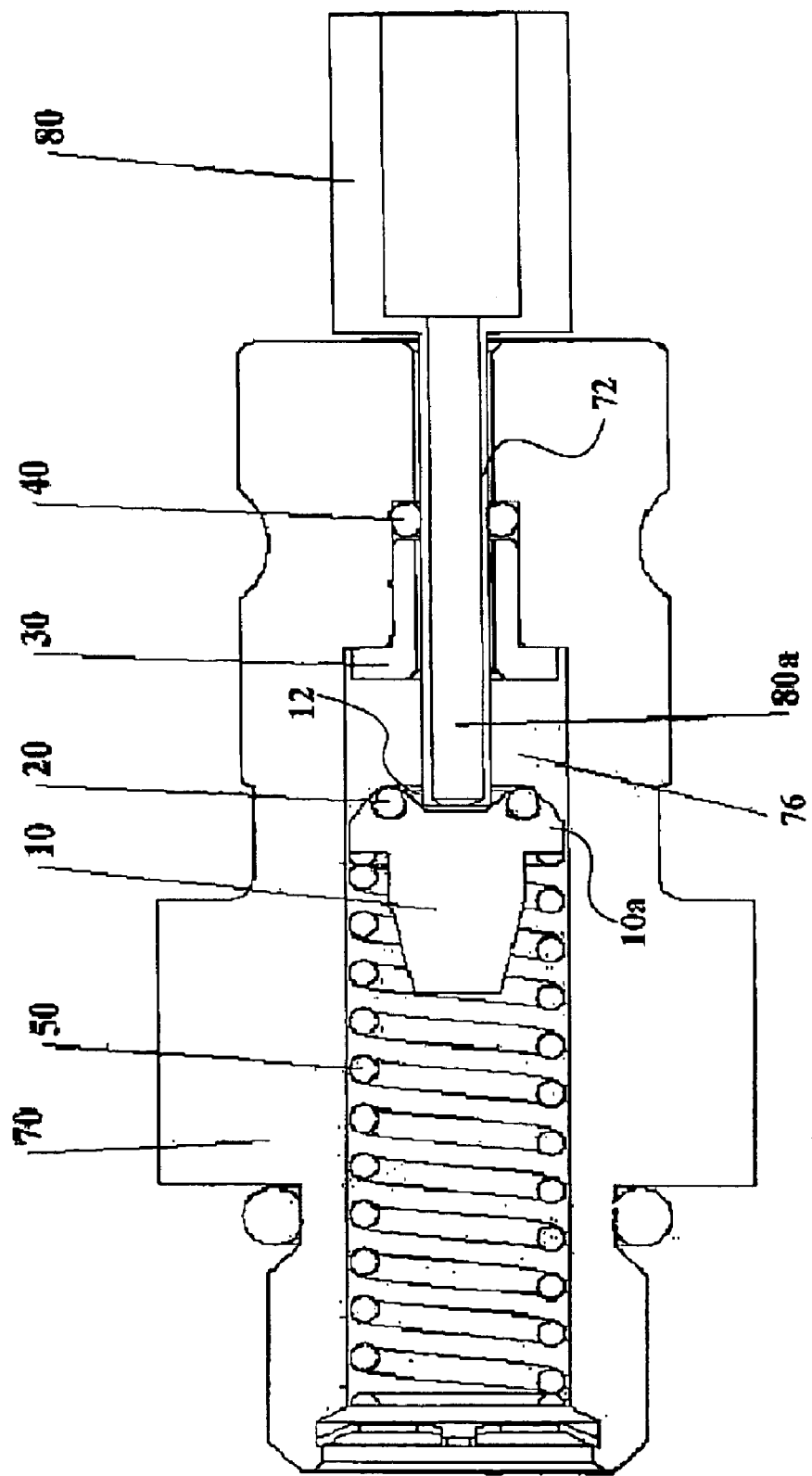
FIG. 2 illustrates the valve system of FIG. 1 with the valve open.
Figure 2A:
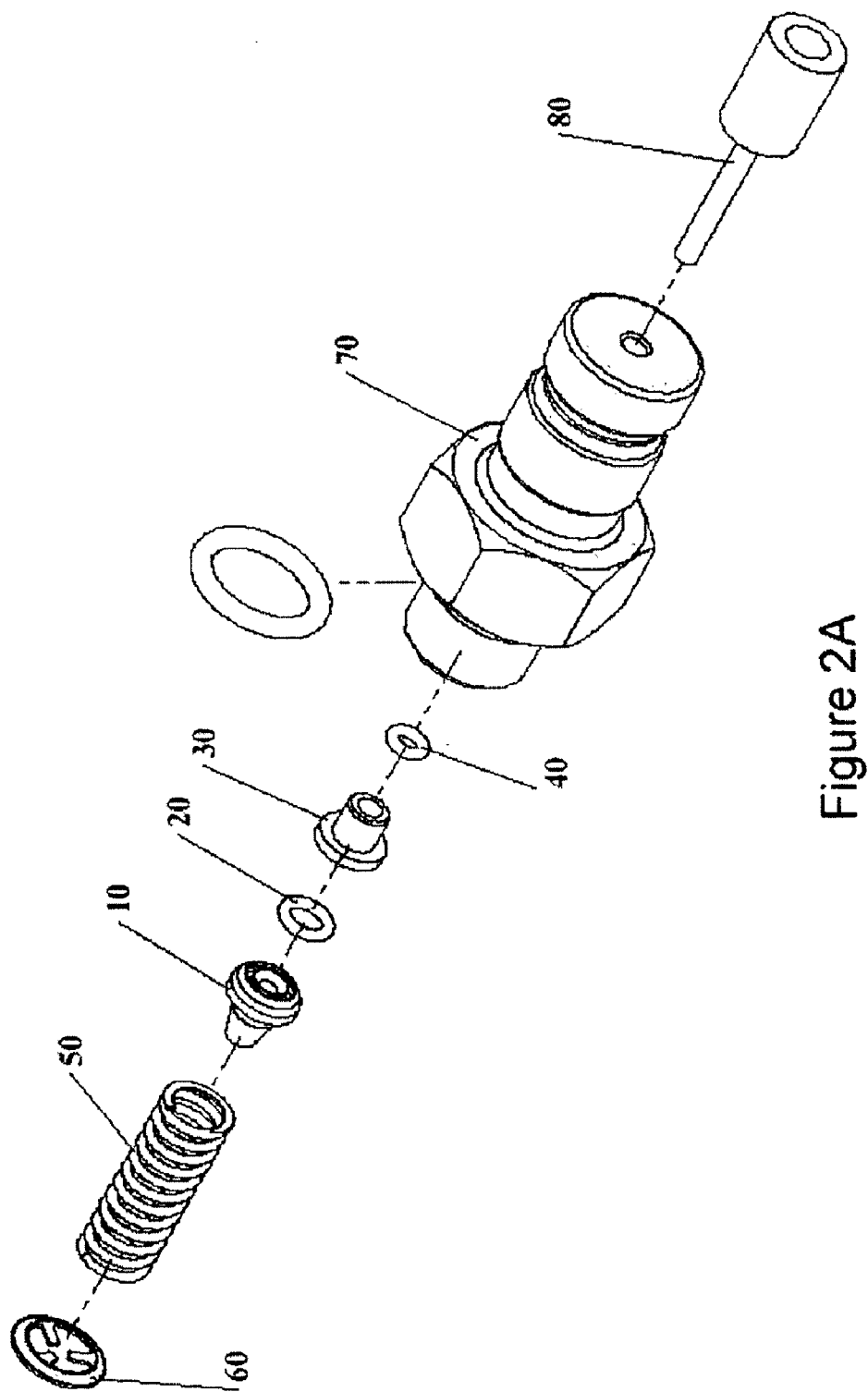
FIG. 2a is an exploded view of the valve system of FIG. 2.

According to FIG. 2, a conventional probe 80 is used to open the valve system for collection or on line analysis. The probe 80 can be hand held and inserted by hand. Alternatively, the probe 80 can be inserted using mechanical advantage, for example, by engaging a threaded exterior portion of the shell (shown in FIG. 4) and a corresponding internal thread of a collar into which the probe has been press fitted. The probe extension 80a is initially inserted into probe insertion passage 72 and continues past a second sealing element 40. The second sealing element 40 forms a seal around the probe extension 80a to prevent fluid from flowing out of the valve via the probe insertion passage 72. The probe extension 80a then contacts the head 10a of valve sealing member 10 here recess 12 facilitates alignment of the probe extension 80, and the valve member 10. The application of further pressure to the inserted probe 80 overcomes the biasing force of the spring 50 and the system pressure and forces the valve seating member 10 away from the valve seat formed on the insert 30 to allow the fluid medium in the system to flow from the cylinder 76 of the valve into a passageway of the probe extension 80a via a side port (not shown) or end notch (not shown) in the probe extension 80a. The second sealing element 40 prevents the fluid medium from escaping around the side of the probe extension 80a even while the valve is held open.

FIG. 3 illustrates a twin valve system which allows the insertion of a probe to allow fluid sampling but also conforms with standards to allow, for example, the determination of pressure within the system using a second valve system. This twin valve arrangement includes a second valve system which is formed by a valve element 90, a valve sealing member 10, and a spring 50. An annular stop washer 60, for the spring 50, is provided in the nipple shell 70. Both valve systems share the same said spring, thus ensuring that opening one valve system will not open the other valve system.

Figure 4:
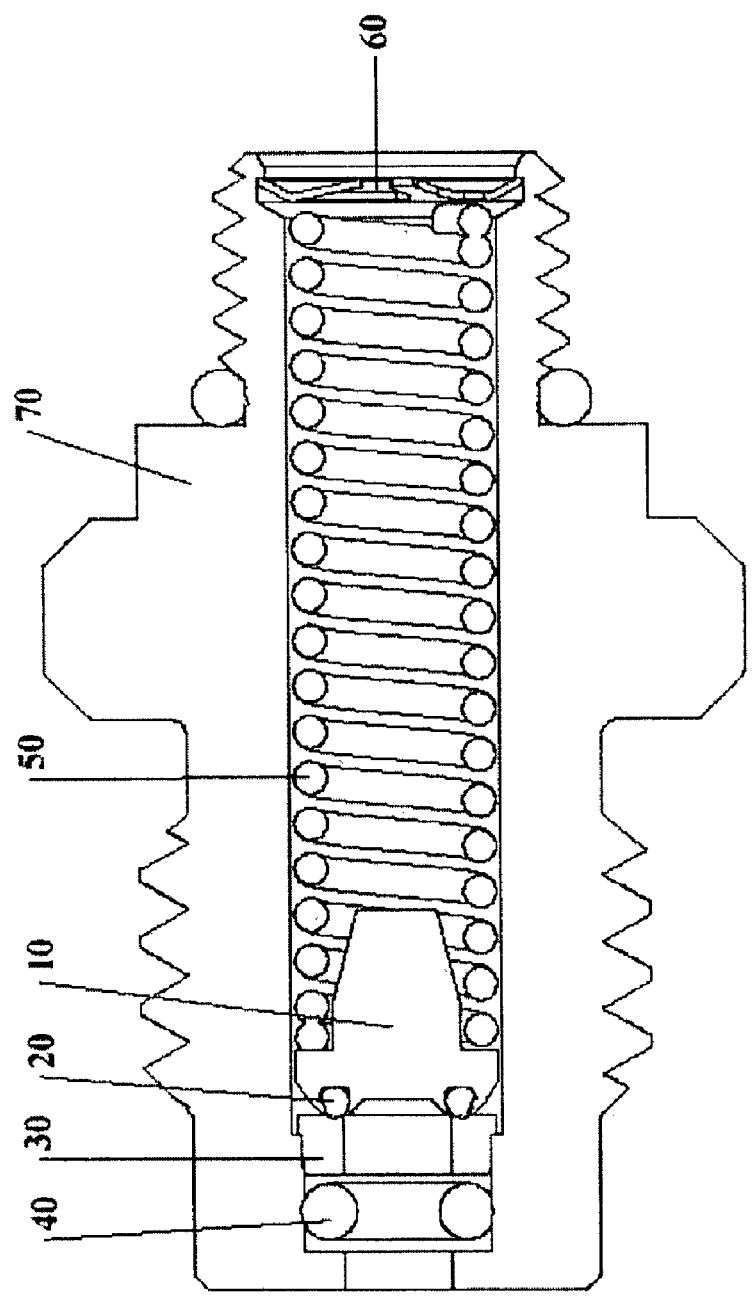
FIG. 4 illustrates a longitudinal view of a valve system according to a threaded embodiment of the present invention.
Figure 4A:
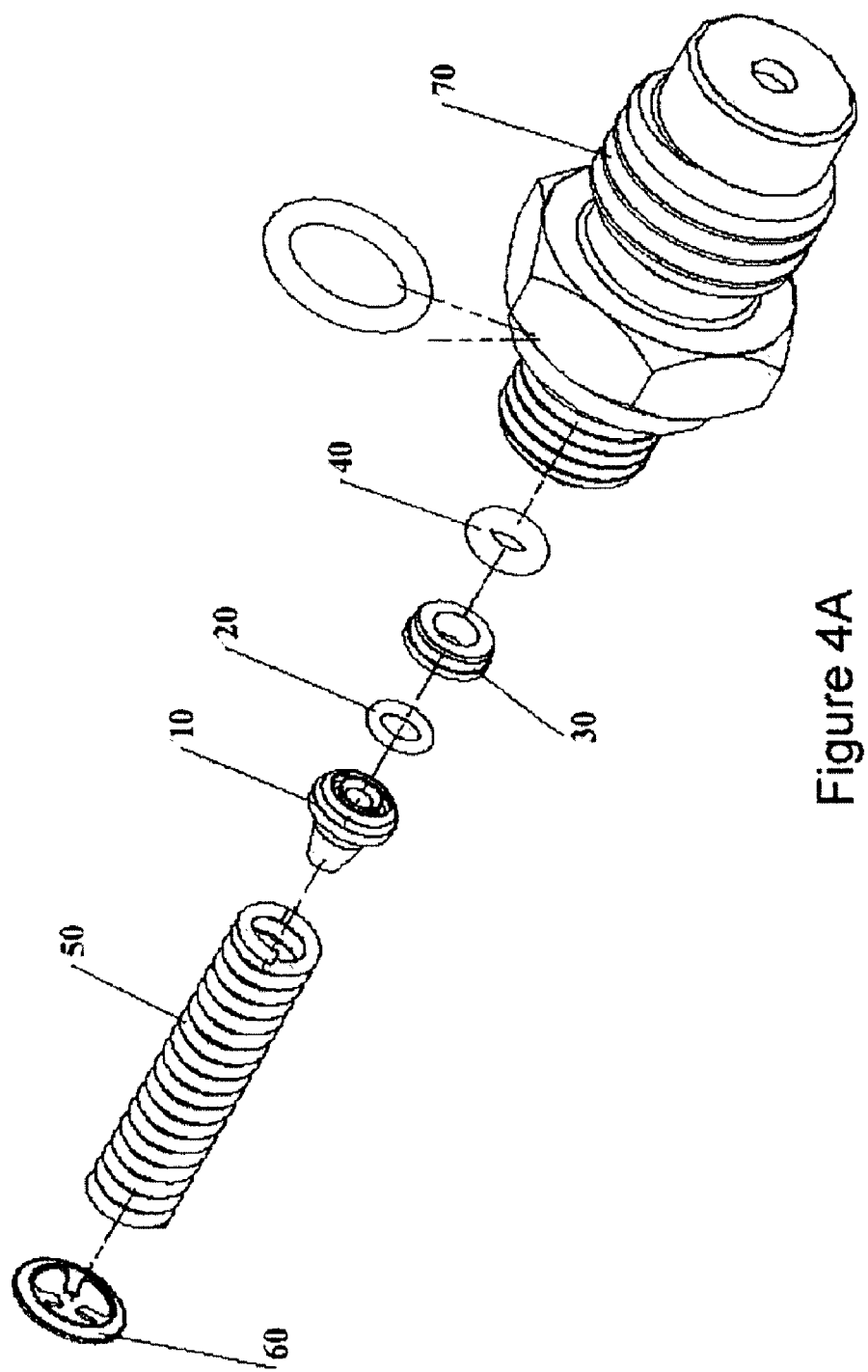
FIG. 4a is an exploded view of the valve system of FIG. 4.

In FIG. 4 the shell part of the nipple 70 is indicated with a threaded coupling profile, in contrast to FIGS. 1,2,3, and 5 where the shell part of the nipple 70 is indicated with a quick action profile.

Figure 5:
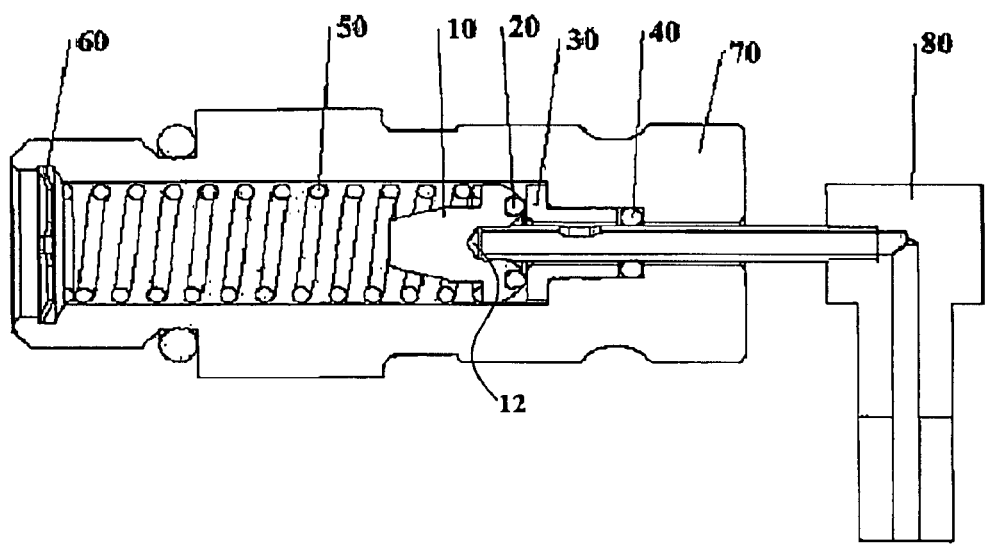
FIG. 5 illustrates a longitudinal view of a valve system according to a "push button" style embodiment of the present invention.
Figure 5A:
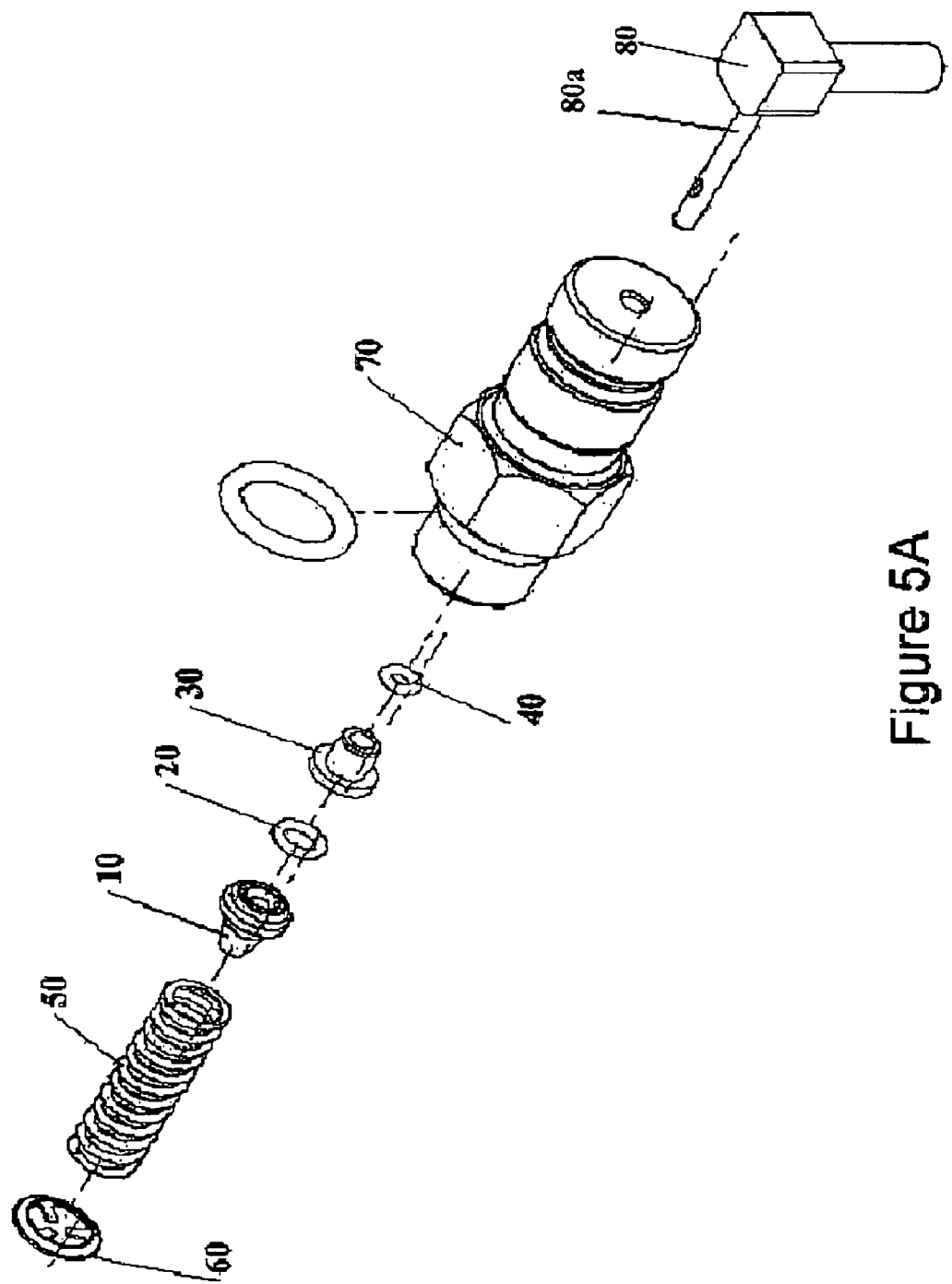
FIG. 5a is an exploded view of the valve system of FIG. 5.

FIG. 5 illustrates a further embodiment in which the probe extension 80a is permanently attached to the valve sealing member 10, allowing the valve to be activated simply by pressing in the probe 80. The recess 12 is formed deeper to hold the end of the probe extension 80a, for example, by a press fit or frictional engagement. Alternatively, the probe 80 can be held by any suitable means including, for example, threaded engagement, welding, soldering and bonding.

FIG. 6 illustrates a still further embodiment of the present invention which is arranged so that the components of the valve system can be assembled into the shell 70 on the side of probe entry. This is in contrast to FIGS. 1 to 5 which show a valve system which has been assembled from the system side. In place of annular washer 60 used in previous embodiments, valve element 80a is used to retain the illustrated components shell 70.

All components, besides the sealing elements are preferably comprised of metals such as steel, copper alloy, brass, stainless steel, aluminum, titanium or plastics such as polyamide or carbon fiber reinforced plastic. The sealing elements may include nitrile (NBR), fluorocarbon (FKM), fluoroelastomers (FFKM), ethylene propylene (EPDM), or polytetrafluoroethylene (PTFE).

Although the above examples discuss the use of the probe activated valve system of the present invention in the context of fluid collection using the probe, the probe activated valve system of the present invention can also be used to introduce fluid from the probe (which is attached, for example, to a pressurized reservoir) to the valve passage. This can, for example, be a method of using the sampling port to introduce fluid into the system.

Alterations, modifications and variations may be effected to the particular embodiments by those of skill in the art without departing from the scope of the invention, which is defined solely by the claims appended hereto.

What is claimed is:

1. A probe activated high pressure sampling valve system comprising:
   a shell having a valve passage, the valve passage having both an axis and an end through which the valve passage is fluidly connected to a probe passage;
   a valve seal at the end of the valve passage, the valve seat having a face transverse to the axis of the valve passage;
   a valve sealing member having a face transverse to the axis of the valve passage,
   a deformable sealing member circumferentially compressed and retained in an annular groove protruding from one of the valve seat face or the valve sealing member face, so that the deformable sealing member is compressed in the annular groove to expose only a small portion of me deformable sealing member;
   the valve sealing member moveable from a closed position in which the deformable sealing member is compressed between the face of the valve sealing member and the face of the valve seat to form a face seal between the parallel faces of the valve seat and the valve sealing member to prevent fluid in the valve passage from flowing to the probe passage, to an open position, upon insertion of a probe to engage and displace the valve sealing member along the axis of the valve passage, such that the face of the valve sealing member is spaced from the face of the valve seat allowing fluid in the valve passage to flow at high velocity from a high pressure zone, having a pressure of up to about 7500 psi, to a low pressure zone, having a pressure as low as atmospheric pressure, in the probe passage for collection by the probe.

2. The probe activated valve system of claim 1, wherein the valve seat is a stop integrally formed on the shell.

3. The probe activated valve system of claim 1, further comprising an insert member provided at the end of the valve passage, the insert member having a head, the valve seat being provided on the head.

4. The probe activated valve system of claim 1, further comprising biasing means normally urging the valve sealing member to the closed position.

5. The probe activated valve system of claim 1, wherein the retained sealing member comprises an elastomeric material.

6. The probe activated valve system of claim 5, wherein the retained sealing member is an O-ring.

7. The probe activated valve system of claim 1, wherein the deformable sealing member is circumferentially retained in the annular groove by mechanical forming.

8. The probe activated valve system of claim 7, wherein the deformable sealing member is circumferentially retained in the annular groove by coining.

9. The probe activated valve system of claim 7, wherein the deformable sealing member is circumferentially retained in the annular groove by rolling.

10. The probe activated valve system of claim 7, wherein the deformable sealing member is circumferentially retained in the annular groove by a pressing operation.

11. The probe activated valve system of claim 4, wherein the valve system works inline with a second valve system controlling the main passage creating a twin valve system, both valve systems utilizing the same biasing means.

12. The probe activated valve system of claim 1, further comprising a recess in the valve-sealing member for aligning the inserted probe with the valve sealing member.

13. The probe activated valve system of claim 1, wherein the probe is permanently fixed to the valve sealing member.

14. The probe activated valve system of claim 13, wherein the probe is permanently fixed to the valve sealing member by frictional engagement with a recess in the valve sealing member.

15. The probe activated valve system of claim 13, wherein the probe is permanently fixed to the valve sealing member by threaded engagement with a recess in the valve sealing member.

16. The probe activated valve system of claim 4, wherein the valve sealing member and biasing means prevent activation of the valve system by manual forces alone without mechanical advantage against a potentially unsafe system pressure.

17. The probe activated valve system of claim 1, wherein the shell comprises threaded means for cooperation with corresponding threaded means on a collar to activate the probe, by means of mechanical advantage to allow high pressure fluid in the valve passage to flow to the probe passage.

18. A probe activated high pressure sampling valve system comprising.
  a shell having a valve passage, the valve passage having both an axis and an end through which the valve passage is fluidly connected to a probe passage, the valve seat having a face transverse to the axis of the valve passage;
  a valve seat at the end of the valve passage;
  a valve sealing member having a face transverse to the axis at the valve passage;
  a deformable sealing member circumferentially compressed and retained in an annular groove protruding from one of the valve seat face or the valve sealing member face, so that the deformable sealing member is compressed in the annular groove to expose only a portion of the sealing member less than about 20% of the circumference of the deformable sealing member;
  the valve sealing member moveable from a closed position in which the deformable sealing member is compressed between the face of the valve sealing member and the face of the valve seat to form a face seal between the parallel faces of the valve seat and the valve sealing member to prevent fluid in the valve passage from flowing to the probe passage, to an open position, upon insertion of a probe to engage and displace the valve sealing member, along the axis of the valve passage, such that the face of the valve sealing member is spaced from the face of the valve seat allowing fluid in the probe passage to flow to the valve passage.

19. The probe activated valve system of claim 1 wherein the deformable sealing member is compressed into the annular groove to expose a portion of the sealing member of less than about 20% of the circumference of the deformable sealing member.

* * * * *